(12) United States Patent
Lourenco et al.

(10) Patent No.: US 9,783,830 B2
(45) Date of Patent: *Oct. 10, 2017

(54) PROCESS FOR MICROBIAL FERMENTATION OF SUGARY SUBSTRATES AND USE OF THE HYDROGEN IN ATOMIC, IONIC OR GASEOUS STATE IN SAID PROCESS

(71) Applicants: Mahle Metal Leve S/A, Jundiai-Sp (BR); LSDATA PLM Software Ltda-ME, Sao Paulo (BR); Advel Tecnologia E Comercio LTDA. EPP, Sumare (BR)

(72) Inventors: Antonio Pedro Lourenco, Sertaozinho (BR); Masayuki Kawakami, Sao Paulo (BR); Jose Francisco Lopes, Sumare (BR)

(73) Assignees: Mahle Metal Leve S/A (BR); LSDATA PLM Software LTDA-ME (BR); Advel Technologia E Comercio LTDA, EPP (BR)

( * ) Notice: Subject to any disclaimer, the term of this patent is extended or adjusted under 35 U.S.C. 154(b) by 0 days.

This patent is subject to a terminal disclaimer.

(21) Appl. No.: 14/916,110

(22) PCT Filed: Aug. 29, 2014

(86) PCT No.: PCT/BR2014/000300
§ 371 (c)(1),
(2) Date: Mar. 2, 2016

(87) PCT Pub. No.: WO2015/027306
PCT Pub. Date: Mar. 5, 2015

(65) Prior Publication Data
US 2016/0201090 A1    Jul. 14, 2016

(30) Foreign Application Priority Data
Sep. 2, 2013 (BR) .......................... 1020130224340

(51) Int. Cl.
*C12P 7/06*    (2006.01)

(52) U.S. Cl.
CPC ................ *C12P 7/06* (2013.01); *Y02E 50/17* (2013.01)

(58) Field of Classification Search
CPC ..................................................... Y02E 50/17
See application file for complete search history.

(56) References Cited

U.S. PATENT DOCUMENTS

| | | |
|---|---|---|
| 8,377,665 B2 | 2/2013 | Barker et al. |
| 2006/0005873 A1 | 1/2006 | Kambe et al. |
| 2006/0123799 A1 | 6/2006 | Tateyama et al. |
| 2012/0297755 A1 | 11/2012 | Adldinger et al. |
| 2013/0217089 A1 | 8/2013 | Hafez |
| 2014/0000670 A1 | 1/2014 | Oesterle et al. |
| 2014/0158178 A1 | 6/2014 | Wong et al. |

FOREIGN PATENT DOCUMENTS

| | | |
|---|---|---|
| DE | 102009058550 A1 | 1/2011 |
| DE | 102012208295 A1 | 12/2012 |
| DE | 102012210627 A1 | 12/2013 |

OTHER PUBLICATIONS

Schroder et al. Angew. Chem. Int. Ed., 2003, 42:2880-2883.*
Steinbusch et al. Bioelectrochemical Ethanol Production through Mediated Acetate Reduction by Mixed Cultures, Environ Sci. Technol, 2010, 44, 513-517.
Jeon, Bo Young et al, Improvement of Ethanol Production by Electrochemical Redox Combination of Symomanas Mobilis and *Saccharomyces cerevisiae*, Department of Biologicial Engineering, Seokyeong University, Apr. 19, 2009.
Castro, Teixieira, J.A, et al. "The Effect of the Electric Field on Lag-Phase, Ethanol and B-Galactosidase Production of a Recombinant S. Cerevisiae Growing on Lactose", 2005.
German Search Report 10 2014 219 852.6, dated Sep. 28, 2015.
Columbian Office Action No. 6998 with a notification dated May 16, 2017 for Application No. 16053967.

* cited by examiner

*Primary Examiner* — Bin Shen
(74) *Attorney, Agent, or Firm* — Fishman Stewart PLLC (57) ABSTRACT

A process for microbial fermentation of sugary substrates may include inoculating hydrogen into a microorganism of a genera fungus or a bacterium present in suspension in a wort under fermentation or in an immobilized bed. The wort under fermentation or in the immobilized bed may contain sugars and microorganisms.

19 Claims, 4 Drawing Sheets

PROCESS FOR MICROBIAL FERMENTATION OF SUGARY SUBSTRATES AND USE OF THE HYDROGEN IN ATOMIC, IONIC OR GASEOUS STATE IN SAID PROCESS

CROSS-REFERENCE TO RELATED APPLICATIONS

This application claims priority to Brazilian Patent Application No. BR 10 2013 022434 0, filed Sep. 2, 2013, and International Patent Application No. PCT/BR2014/000300, filed Aug. 29, 2014, all of which are hereby incorporated by reference in their entirety.

TECHNICAL FIELD

The present invention relates to a biochemical process for selectively increasing the production of alcohol through microbial fermentation of sugars.

Particularly, suitable concentrations of hydrogen are inoculated into the microorganisms in process, and this can take place in a continuous, semicontinuous or batch production regime, said process comprising sugary wort, microorganisms of the genus fungus or bacterium, with naturally occurring or especially selected or adapted characteristics, or characteristics of recombinant, flocculating lines, in suspension in the wort under fermentation or in an immobilized bed and in micronutrients.

BACKGROUND

Alcohols are organic compounds having the functional hydroxyl group (—OH) attached to one or more saturated carbons, containing one or more carbon atoms. The best known compound of this class is ethanol or ethyl alcohol. The latter can be found in alcoholic beverages, in cleaning products, in pharmaceutical products, such as chemical solvent and also in its most voluminous application as fuel for internal combustion engine.

More than 90% of ethanol is produced worldwide from fermentation of sugars coming from direct sources such as sugar-cane, molasses and fruit pulps, or obtained directly by hydrolysis of starch and cellulose. In these amylaceous, feculent and cellulosic groups, a wide variety of grains stand out, such as corn, manioc, other tubercles, sorgo, wheat, barley, sugar-cane bagasse, potato, whey, etc.

The manufacture of ethanol by fermentation and distillation is basically divided into 4 phases: preparation of the raw material or saccharification, liquefaction, fermentation and distillation. For the productions of wine and beer there is no distillation phase. The preparation of the raw material, such as grinding, crushing and leaching, comprises passing the source of sugar, starch or cellulose through processors. In the second phase, one obtains diluted substrates that can either be processed in the fermentation or passed through other intermediate processing of breaking the amylaceous or ellulosic chains into sugar molecules by effect of hydrolysis. The sugary juice or wort obtained is led to fermentation.

The fermentation phase comprises adding microorganisms, fungi or bacteria, which transform the sugars into alcohol by a number of enzymatic reactions. After this process, on industrial scales, which are characterized by periods of fermentation as shown in Table 1, the fermented wort or wine is obtained.

TABLE 1

Typical periods of processes for alcoholic fermentations

| | |
|---|---|
| Wine | Weeks |
| Beer | Weeks |
| Alcohol - generic production | From 10 hours to a few days |
| Fuel alcohol - Brazil | From 4 to 12 hours |

The wine then follows to the fourth and last step, the fractionated distillation, giving rise to hydrated or anhydrous alcohol, depending on the desired and employed characteristics of distillation process and dehydration.

The step that affects the result of the production of alcohol more directly and, therefore, one of the most studied is fermentation, called also alcoholic or ethylic fermentation, in the case of the "rota etilica" (ethylic pathway), which is the biochemical process of transforming sugars such as polysaccharides and monosaccharides such as trioses, tetroses, pentoses and hexoses, among which sucrose, glucose, fructose and xylose stand out, into alcohol. In this process, microorganisms that are responsible for conversion of sugars into molecules of pyruvic acid or pyruvate participate, in a number of intracellular enzymatic reactions, usually called glycolytic pathway. Subsequently, in anaerobic conditions, two other enzymatic reactions take place, which characterize the fermentative process. The first reaction, decarboxylation of the pyruvate, is performed by the enzyme pyruvate decarboxylase, by means of which the carboxyl group is eliminated from the pyruvate molecule, converting it to acetaldehyde molecule, with release of carbon dioxide. The second reaction is the reduction of the ethanol acetaldehyde, performed by the enzyme alcoholic dehydrogenase, completing the fermentative reaction proper.

In general, the fermentative processes are characterized in that they combine substrates, types and strains of microorganisms and especially adequate operational conditions, with a view to maximize the process yield and special characteristics to be transferred to the wort under fermentation, since it is subject to various conditions, both fermentation activating and inhibiting conditions, with the consequent interference in the efficiency and in the quality of the process itself.

The main features that characterize all the reactions, regardless of their being are chemical or enzymatic, are those related to the conversion factors, or more specifically to the efficiencies or yields of these conversions. Evolving from the conception of the spontaneous generation theory, alcoholic fermentation has undergone experimental evaluations and theoretic considerations, being regarded as one of the most successful processes by the prior art. Coupled to the cellular nature of the microorganisms, chiefly of fungi, as eukaryotic single-celled organisms, like cells of animal nature, the study and understanding thereof have been privileged as a means of easy experimental access, in the aerobic and anaerobic respiratory processes, the latter being known also as alcoholic and lactic fermentation, and develop freely.

In 1810, Louis Joseph Gay-Lussac formulated the stoichiometric equation that related the production of ethanol and carbon dioxide from alcoholic fermentation of glucose, which is known to date as:

(equation (1))

In 1863, Louis Pasteur introduced the concept and action of microorganisms responsible for conversion of glucose (monosaccharide) to ethanol and carbon dioxide. Thirty-four years later, in 1897, Eduard Buchner fermented sugar at the laboratory without using live microorganisms, introducing the concept of enzymatic action of the fermentative process, illustrated below:

Zymase refers to an enzymatic complex that catalyzes the fermentation of sugar to ethanol and carbon dioxide.

Thus, Buchner presented the hypothesis that yeast cells secreted proteins in the medium, bringing about the fermentation of sugar. Later, it was demonstrated that these fermentation reactions took place inside the yeast cell.

Figure 1:
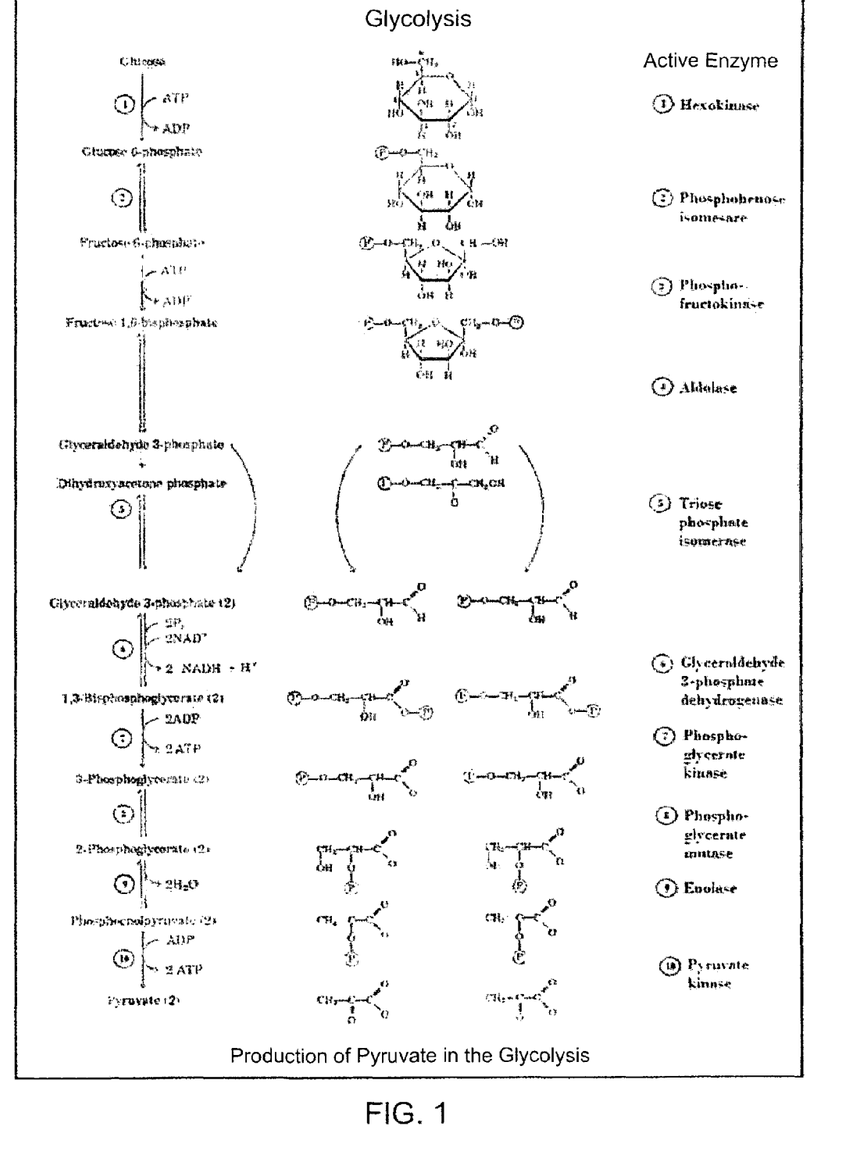
FIG. 1 refers to refers to the glycolytic pathway (glycolysis) of the prior art, which takes place in the cytoplasm of a microorganism or eukaryotic or prokaryotic cell, in the processing of glucose, comprising the lasts steps of this sequence, the production of pyruvate.
Figure 2:
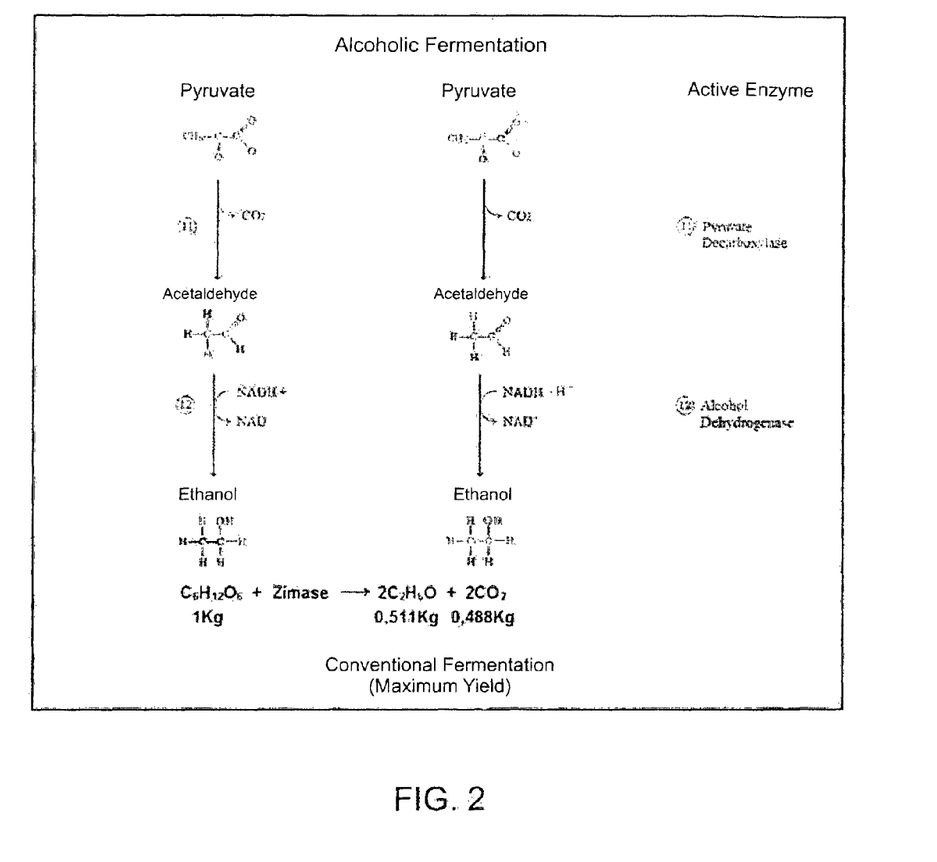
FIG. 2 schematizes the alcoholic fermentation reactions involved in a prior-art fermentation process where each pyruvate molecule, through the pyruvate decarboxylase, undergoes release of the carboxyl and the consequent release of a carbon dioxide molecule and an acetaldehyde molecule, the latter being transformed to ethanol by the action of the enzyme alcoholic dehydrogenase.

All this development is in agreement with the nature of the efficiency or yield of the transformation of sugars into alcohol, by the verification that, in the natural fermentation conditions, a glucose molecule could produce up to two ethanol molecules and two carbon dioxide molecules. This understanding is quite known as Gay-Lussac (G-L) Yield, its maximum value in the fermentation of glucose being of 51.1% (mass/mass). FIGS. 1 and 2 illustrate the sequence of reactions and the maximum massic yield in the fermentation of glucose.

For the purposes of comparisong, the simplified equations for fermentative process yields of pentoses, hexoses and disaccharide (sucrose) are shown belor. The disaccharide sucrose is the predominant sugar in sugar-cane.

Invertase refers to an enzyme that catalysis the hydrolysis of sucrose in hexose, fructose and glucose, the mixture of which is also called inverted sugar syrup.

In the alcohol industry by fermentation of sugars, the pursuit of greater process yields is a constant, involving complete and complex studies and experiments in the physicochemical and biological domains. In a general way, one may write the equation for the complete treatment of the alcoholic fermentation process from the point of view of efficiency ore alcoholic yield as follows:

[Sugar]+[Microorganisms]→[Ethanol]+[CO2]+[B-products]+Energy

Herein one understands as maximal real yield the quotient between the concentration of ethanol produced [Ethanol] by the concentration of sugar [Sugar] consumed in the conversion.

During the fermentation process, various microorganism natures may contribute to the consumption of sugar, such as yeast, other than fungi and bacteria. These microorganisms consume the sugary substrate for cellular growth of the species and also in the production of by-products such as acids and higher alcohols, turning to parasitic processes and causing reductions in the fermentation yield.

In 1937, Firmin Boinot patented in France and in 1941 he obtains the U.S. Pat. No. 2,230,318 for a process of carrying out industrial alcoholic fermentations. In the Thirties this process arrives in Brazil, contributing markedly to the increase of fermentation yield, which is now widespread in the world and known by the process name Melle-Boinot, and chiefly but not exclusively applied to fermentations with yeast. A merit of this process is the direct con concurrent reduction of sugar, provided by reuse of the microorganisms and by the treatment and recycle thereof, by centrifugal separation, followed by an acidic treatment for periods of two to four hours in a medium with pH of 2 to 3, in concentrated form, which promotes the drastic reduction of the bacterial population. After this treatment, the yeast milk, as the centrifuged yeast is called, concentrated and treated, if returned to the process. This operation may bring about a sugar consumption reduced to less than 1% (one percent) of the sugar available.

Carbon dioxide as the products released in the decarboxylation of pyruvate is considered as a parallel product of the fermentative process.

Besides the by-products resulting from parasitic processes, as discussed above, other products are generated during the alcoholic fermentation, such as: glycerol, organic acids (succinic, acetic, pyruvic acids, and others) and higher alcohols, acetaldehyde, acetoin, butyleneglycol and other compounds. It is estimated that from 3% to 5% (three to five percent) of the sugar available in the process are consumed in these conversions.

In energetic terms, illustratively, in anaerobiosis conditions, the yeasts deviates its metabolism to the alcoholic fermentation, the ethanol and carbon dioxide being only the two excreta of the whole process. Thus, it follows that:

$C_6H_{12}O_6 + 2Pi + 2ADP \rightarrow 2C_2H_5OH + 2CO_2 + 2H_2O + 2ATP$ ($\Delta G_0 = -56$ kcal/mole)

On the other hand, in aerobiosis conditions, particularly in the cellular multiplication phase, the yeast carries out respiration. Unlike the fermentation that takes place in its cytoplasm, the respiration, which takes place in the mitochondria, leads to the formation of an amount of ATP (Adenosine Triphosphate) (the energetic exchange means) nineteen times as big as that obtained in the alcoholic fermentation, as illustrated below:

$C_6H_{12}O_6 + 6O_2 + 38Pi + 38ADP \rightarrow 6CO_2 + 38ATP + 6H_2O$ ($\Delta G_0 = -686$ kcal/mole)

Many actions are still taken during the fermentation process, as initiatives to reduce the consumption of sugars in parasitic processes and undesirable by-products. Control of Ph and temperature of the wort under fermentation, as well as the control of micronutrients and contaminants present, are variables that assume important positions in the process and can stimulate or inhibit the biochemical dynamics.

The low pH of the medium (pH<4.0), particularly associated to high operation temperatures (Top>38° C.), proves to be the factor of greatest physiological interest for the yeast obtained and used at units of industrial production of ethanol, when compared with other inhibitors such as sulfite, lactic acid, alcoholic contents and high concentrations of sugars). The pH 4.5 of the wort, with temperature ranging from 20° C. to 37° C., enables protection against stress factors, and one obtains a higher viability of cell, sprouting, alcoholic yield, regular morphology of the yeasts, decrease in residual sugar and lower release of amino acids in the medium, providing better alcoholic efficiency and stability of the process.

As to the nutrition, the yeast is a heterotrophic microorganism, which feed by absorption. The main nutrients, necessary to the development of the yeasts, so that a satisfactory fermentation can take place, are: (i) nitrogen, a plastic transformation element, important to the growth of the yeast; (ii) phosphorus, energy translocation element—in the absence thereof no fermentation will take place; (iii) potassium, (iv) magnesium; (v) zinc; (vi) manganese, all of which are important in enzymatic reactions; vitamins of the B complex, which are fermentation accelerators, besides the presence of other salts, such as cobalt, copper, sulfur, boron, which are referred-to as micronutrients.

Yeast is also a saprophytic microorganism, which requires an elaborate source of carbon—glucose or another sugar, which supplies chemical energy and the carbonic skeleton of its cellular structures, constituted predominantly by carbon, oxygen and hydrogen. Some vitamins, such as thiamine and pantothenic acid, are also demanded.

As to the source of nitrogen, the yeast uses this element in the ammoniacal (NH4+), aminic (urea) or aminic (in the form of amino acids) forms, with no metabolic capability to make use of nitrate and little or no capability of using proteins from the medium. Since the ammoniacal form is the main one, in the absence thereof the yeast looks for other forms, such as amino acids, thereby causing an increase in the production of secondary components, such as isoamyl, amyl, propyl, isopropyl, butyl, isobutyl alcohols. Phosphorus is absorbed in the form of ion H2PO4-, the predominant form at pH 4.5, whereas sulfur can be assimilated from sulfate, sulfite or thiosulfate. With the use of sulfuric acid in the treatment of yeast, however, as presented above, or in the use of molasses in mixed wort, one avoids the additional use of sulfur, which is lethal to the microorganism when in excess, since present sulfur proves to be sufficient to the process.

On the basis of the foregoing and considering, for instance, the alcoholic fermentation yield with glucose substrate or with directly fermentable sugars, at the maximum theoretical massic G-L yield of 0.511 m/m, according to equation (1), as being 100% maximum theoretic yield, the real fermentative process yield can reach maximum values ranging from 92% to 94% and, moreover, in the most aseptic and controlled productive environments. In unites of lesser control and asepsis, this value may be lower than 85%, which means considerable losses in the productive process.

In this regard, one continuously seeks all and every increase in efficiency, focusing on improved and adequate operational controls, strains and natures of microorganism, selected, combined and modified, with higher productivity and more process resistances. Increases in the fermentative yield of 0.1% to 0.5% already justify considerable investments, in view of the high numbers related to alcoholic production in these industrial media.

Various papers have been developed to improve the yield of a process for producing ethanol, as exemplified hereinafter:

Document U.S. Pat. No. 4,451,566 describes methods and apparatus for the enzymatic production of ethanol from fermentable sugars. A sequence of enzymes for the catalysis of the conversion of sugars into ethanol is retained in a diversity of reaction zones. The fermentable sugar solution passes sequentially through these zones, and the alcohol is recovered in the last zone. In spite of providing a more efficient reaction that the usual process, the present document provides an expensive, complex and difficult-to-maintain solution.

Patent application WO 2007/064546 describes a process for improving the yield of ethanol, decreasing the fermentation time and reducing the formation of by-product by monitoring and controlling the oxy-reducing potential of the fermenter. However, this process requires very specific and difficult-to-maintain monitoring due to the high costs involved, impairing the industrial application of this solution.

Patent document WO 2008/024331 describes a method for magnetic fermentation that includes subjecting a biological material to a static magnetic field for carrying out fermentation of the biologic material in a fermented product. The fermentation reaction may occur in an alkaline or acidic medium, and the magnetic field may be positive or negative. The present document makes use of the static magnetic field to provide an environment more suitable for cell reproduction of the microorganisms. In spite of increasing the number of microorganisms in the alcoholic fermentation, thus increasing the reaction yield, this process needs constant monitoring and total control over the reaction, which makes it excessively expensive and, therefore, economically unfeasible for industrial application.

The prior art also discloses methods for improving the efficiency of carbon capture, as described in U.S. Pat. No. 8,377,665. This method comprises bacterial fermentation, using gaseous substrates according to the Wood-Ljungdahl pathway, which comprises a sequence of enzymatic reactions that take place in bacterial lines.

Although there are many bibliographic references that describe fermentative processes to improve the yield of the production of ethanol, the prior art does not describe specifically the action of hydrogen in a metabolic fermentation process for the purpose of selective production, this process constituting an innovative and original technology. Moreover, all the processes developed have sought the increase in the real yield up to the theoretical limit of the G-L yield.

SUMMARY

The present invention has the objective of providing a process for microbial fermentation of sugary substrates, which comprises inoculating hydrogen into the microorganisms of the genera fungus or bacterium, with naturally occurring characteristics, or especially selected or adapted, or of recombinant, flocculating lines, or in suspension in the wort under fermentation or in an immobilized bed.

A second objective of the invention consists in using hydrogen in the ionic, atomic or gaseous state, or a mixture thereof, for inoculation into the microorganisms of the genera fungus or bacterium, with naturally occurring characteristics, or especially selected or adapted, or of recombinant, flocculating lines, or in suspension in the wort, or in immobilized bed, for the selective production of alcohol.

A third objective of the invention consists in establishing an innovative biochemical process for the selective production of alcohol through fermentation of sugars such as polysaccharides and monosaccharides such as trioses, tetroses, pentoses and hexoses, wherein sucrose, glucose, fructose and xylose stand out, with greater utilization of carbon and the consequent increase in the selective production of alcohol, exceeding the theoretic yield of G-L, and reduction in the emission of carbon dioxide in the fermentation.

By "atomic or ionic state" one understands herein hydrogen in the atomic (H) or ionic (H+) form.

By "gaseous state" one understands herein molecular hydrogen (H2).

A fourth objective of the invention consists in establishing an effective and environmentally justifiable process, with greater utilization of the carbon in the conversion of sugars in fermentation in alcohol, besides reducing the emission of carbon dioxide into the environment.

A fifth objective of the invention consists in removing the limit of efficiency for higher levels, altering the cellular metabolism of the microorganisms, without altering them genetically.

By virtue of its simplicity, economicity and efficiency, the process of the present invention can be applied in new industrial units of production, or implemented at already installed structures and units.

The present invention relates to a process for microbial fermentation of sugary substrates, which comprises inoculating hydrogen into the microorganisms of the genera fungus or bacterium present in suspension in the wort under fermentation or in immobilized bed, said wort under fermentation or immobilized bed containing sugary substrates and micronutrients.

The inoculation of hydrogen in atomic, ionic or gaseous state into the microorganisms present in the fermentation takes place by means of at least two electrodes applied directly to the wort under fermentation or immobilized bed with application of voltage in pre-electrolysis regime or in full electrolysis. This hydrogen gas is also produced out of the bioreactor, via electrolysis of water, and in this case the inoculation of the microorganisms takes place via direct gushing into said bioreactor.

The control over hydrogen in atomic, ionic or gaseous state takes place by means of the voltage applied to the electrodes actuating on the wort under fermentation or in immobilized bed, the pre-electrolysis regime voltage ranging from 0.1V to 1.24V, and the full-electrolysis regime voltage ranging from 1.24V to 30V, either in direct current or in alternating current, this latter comprising cycles of 50 Hz to 100 Hz, from 100 Hz to 500 Ha, and from 500 Ha to 1000 Hz.

The present invention also relates to the use of hydrogen in atomic, ionic or gaseous state or mixtures thereof, characterized in that it is for inoculation in the microorganisms present in a fermentative medium containing sugary substrates, such as polysaccharides and monosaccharides like trioses, tetroses, pentoses and hexoses, sucrose, glucose, fructose and xylose standing out, for the selective production of alcohol.

The process described in the present invention consists, therefore, in modifying the massic efficiency limit of production of alcohol to higher parameters, altering the cellular metabolism of the microorganisms without altering them genetically. The hydrogen reducing action, coupled to its ease of permeating the cell membranes of the microorganisms, accessing their internal compartments, cytoplasm, mitochondria and intracellular organelles provide an innovative biochemical process for the selective production of alcohol through fermentation of sugars, bringing about better use of the carbon, with the consequent increase in the alcoholic yield in the fermentation reaction and reduction in the contents of emission of carbon dioxide.

DETAILED DESCRIPTION OF THE FIGURES

As described before, processes for the production of alcohol through fermentation of sugars are already known to those skilled in the art and are universally considered, in their limits of efficiency, by the stoichiometric equation formulated by Gay-Lussa in 1810 (equation (1)). According to this formulation, in the present-day prior art, a Glucose molecule under fermentation is capable of producing, at the most, 2 ethyl alcohol molecules and 2 carbon dioxide molecules, as shown in equation (2).

(equation (2))

C6H12O6 + Zymase ⟶ 2C2H5OH + 2CO2

1 kg          0.511 kg     0.488 kg Conversively, considering the fermentation from sucrose, substantially presente in sugar-cane sugar, one alternatively obtains the equation belos:

(equation (3))

C12H22O11 + H2O + Invertase ⟶

1 kg

4C2H5OH + 4CO2

0.538 kg     0.514 kg

On can see from equations (2) and (3) the condition of maximum massic efficiency of 0.511 (m/m), mass/mass, in the fermentation of glucose, and 0.538 m/m in the fermentation of sucrose. Even by the more recent equation arrangements, which consider the actions of enzymatic reactions, this limit has been considered in the global yield evaluation, in the processes comprised by the present-day prior art.

According to the prior art, in the glycolytic pathway, called also glycolysis, which is the sequence of enzymatic reactions that takes place in the cell cytoplasm of the microorganism, which may be an eukaryotic or prokaryotic single-celled one, in the processing of glucose (sugar with six carbon atoms in the molecule), in the last steps of this sequence there is production of pyruvate:

(ion $H_3C$    $O^-$), acidic, in the molecule of which there are 3 (three) carbono atoms, as shown in FIG. 1. From these reactions, therefore, two pyruvate molecules originated starting from a glucose molecule. Then, in anaerobic regime, in the absence of oxygen, the alcoholic fermentation takes place. In this fermentative process, from each pyruvate molecule, through pyruvate decarboxylase, the release of carboxyl takes place, as well as the consequent release of a carbon dioxide molecule and an acetaldehyde molecule, after which the latter is transformed to ethanol by the action of the enzyme alcoholic dehydrogenase, as shown in FIG. 2. These enzymatic reactions are reversible.

Thus, according to the prior art, there is the relationship of maximum production of two ethanol molecules and two carbon dioxide molecules for each glucose sugar molecule in the alcoholic fermentation process, called also ethylic fermentation.

Thus, the reduction of the carbo group:

which is derived from the union of the carbonyl group:

radical of ketones and aldehydes, with the hydroxyl group (O—H)—, radical of alcohols and phenols, derived by decarboxylation of the two pyruvate molecules by the enzyme pyruvate decarboxylase, in addition to Reducing Equivalents—RE/ER, preferably reduced by the high availability or abundance of hydrogen, results in the formation of an acetaldehyde molecule synthesized through the double carboxyl group, as the product of a new alcoholic fermentation pathway. With the abundance of hydrogen, there is an increase in the concentration of enzymes NADH, NADPH and FADH2, among other important electron carriers in the cytoplasmatic or mitochondrial oxide-reduction processes. The equations below illustrate the oxide-reduction processes of these coenzymes:

Reduction of Coenzyme Nicotinamide Adenine Dinucleotide

NAD++H++2e- ↔ NADH    (equation (4))

Reduction of Coenzyme Nicotinamide Adenine Dinucleotide Phosphate

NADP++H++2e- ↔ NADPH    (equation (5))

Reduction of Coenzyme Flavine and Adenine Dinucleotide

FAD++2H++2e- ↔ FADH2    (equation (6))

Figure 3:
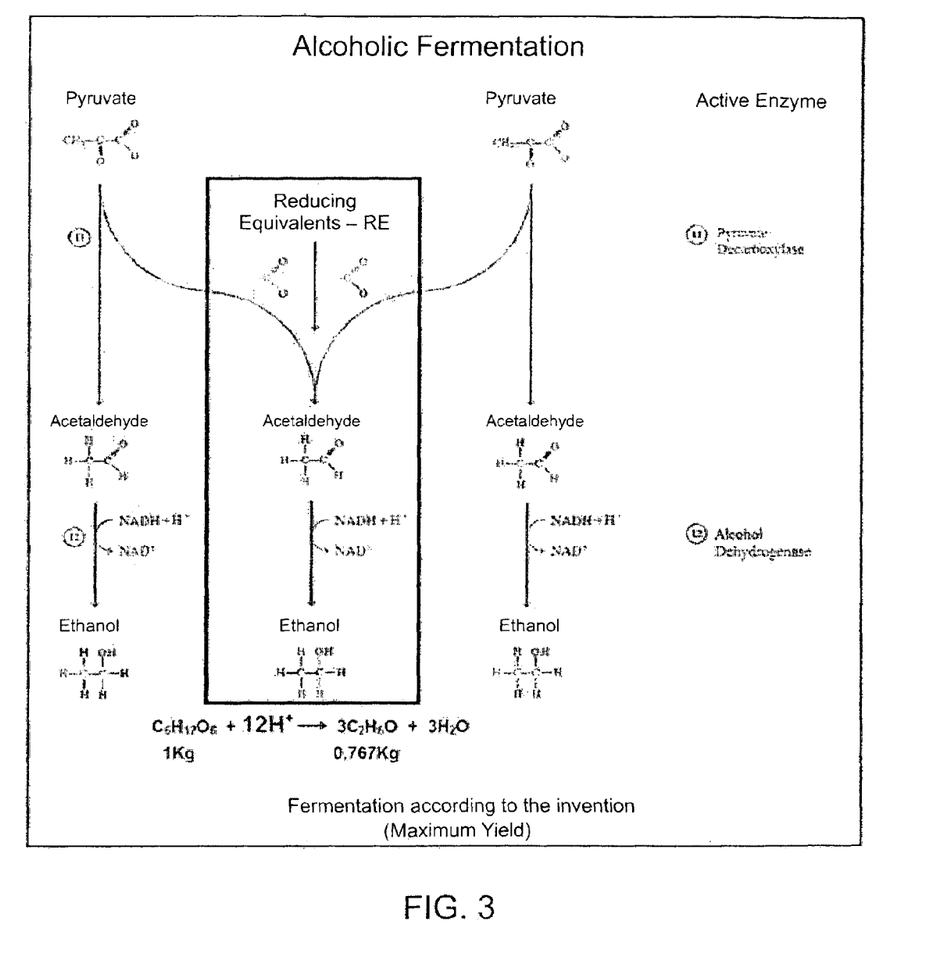
FIG. 3 schematizes the fermentation reactions involved in the process described by the present invention, where the reduction of the carboxyl group with the hydroxyl group, derived by decarboxylation of the two pyruvate molecules, by the enzyme pyruvate decarboxylase, in addition to Equivalent Reducers, preferably reduced by raising the availability of hydrogen, bring about the formation of an acetaldehyde molecule synthesized through the double carboxyl group as the product of a new alcoholic fermentation pathway.

Then the acetaldehyde molecules are reduced to ethanol molecules by the reducing action of the enzyme alcoholic dehydrogenase, as illustrated in FIG. 3.

Thus, the present invention enables one to obtain generic and simplified equations, such as equation (7) below, for the typical concentrations of sugars, hydrogen, microorganism and products obtained in this type of fermentation, such as concentration of ethanol, carbon dioxide and water:

[Sugars]+[H]☐[Microorganism]→☐☐C2H5OH]+ [CO2]+[H2O]    (equation (7)).

The terms "[ ]" denote the respective concentrations of sugars, hydrogen, live microorganism, ethanol, carbon dioxide and water, agents and products of the alcoholic fermentation in the presence of hydrogen, in a typical fermentation reaction of sugary wort, by employing yeast, eukaryotic single-celled fungus. The symbol "☐" aims at illustrating the inoculation of hydrogen into the microorganism.

This inventive principle, together with the generic equation (7), is also applied in fermentations that involve bacteria, prokaryotic cells, with processing of carbohydrates, such as polysaccharides and monosaccharides like trioses, tetroses, pentoses and hexoses, wherein sucrose, glucose, fructose and xylose stand out, with selective production of ethanol or higher alcohols.

By virtue of its simplicity, economy and efficiency, this invention can be either applied at new production units, or implemented at already installed structures and units.

The present invention relates, therefore, to a biochemical process for increasing selectively the yield of the production of alcohol through modifications and improvements in the step of fermenting the solutions containing sugars, employing fermentative microorganisms of the group fungi or bacteria. These improvements consist in inoculating hydrogen in atomic, ionic or aqueous state of mixtures thereof into the microorganisms that participate in the fermentative reaction of the sugary wort.

The present process comprises adding 5%-30% (mass/volume) of sugary substrates, between 5% and 25% (mass/volume) of microorganism. The microorganisms are completed in an automatic and controlled manner as a function of the necessary contents and those available in the wort under fermentation.

For inoculation of hydrogen, a system for generating such hydrogen is required, the system comprising:

(i) supplying a fermentative medium with a pre-electrolysis voltage by means of electrodes, said voltage comprising values lower than the voltage required for occurrence of electrolysis of water in the medium, characterized by the ionic conditions of the wort under fermentation, preferably between 0.1 V and 1.124 V, or]

(ii) supplying the fermentative medium with a full-electrolysis voltage of water, characterized by the ionic conditions of the wort under fermentation, preferably between 1.24 V and 30 V, more preferably between 1.24 V and 20 V, and still more preferably between 1.24 V and 10 V;

(iii) the production of hydrogen out of the reactor takes place via electrolysis of water, with voltage between 1.5 V and 30 V.

The electrodes applied to the fermentative medium comprise at least one cathode and one anode, the cathode and the anode acting preferably directly on the wort under fermentation.

In an embodiment of the invention, the electrodes, anode and cathode, are applied directly onto the microorganisms, in the phase of feeding them to the bioreactor.

In a second embodiment of the invention, the electrodes used in the fermentative medium comprise at least one cathode and one anode, the cathode preferably acting directly on the wort under fermentation, while the anode may be applied on another electrolyte, the latter being alternatively saline, as two electrolytes, with media separated by an ion-permeable separating membrane.

The sugary wort comprises sugars such as polysaccharides and monosaccharides like trioses, tetroses, pentoses and hexoses, wherein sucrose, glucose, fructose and xylose stand out, or mixtures thereof.

In an embodiment of the invention, the fermentative microorganisms of the invention are selected from yeasts of the group of fungus, as of the genus *Saccharomyces* and more specifically the *Saccharomyces cerevisiae* strain and the species of the genus *Schizosaccharomyces pombe, Pichia stipites, Torula, Candida shehatae*, of naturally occurring lines, or especially selected or adapted, or recombinant, flocculating lines, in suspension in the wort under fermentation or in immobilized bed.

In a second embodiment of the invention, the fermentative microorganisms are selected from the group of bacteria, more especially like species of the genera *Zymomonas mobilis, Escherichia coli* and *Clostridium*, of naturally occurring lines, or especially selected or adapted, or of recombinant, flocculating lines, in suspension in the wort under fermentation or in immobilized bed.

In a preferred embodiment, the fermentative microorganism selected comprises the fungus of the species *Saccharomyces cerevisiae*.

In another preferred embodiment, the fermentative microorganism selected comprises the bacterium of the species *Zymomonas mobilis*.

The fermentation wort also admits the addition of micronutrients such as nitrogen, phosphorus, potassium, magnesium, calcium, zinc, manganese, copper, iron, sulfur, cobalt, iodine or mixtures thereof.

The microorganisms are added at contents as variables and should be controlled during the process under demand.

Figure 4:
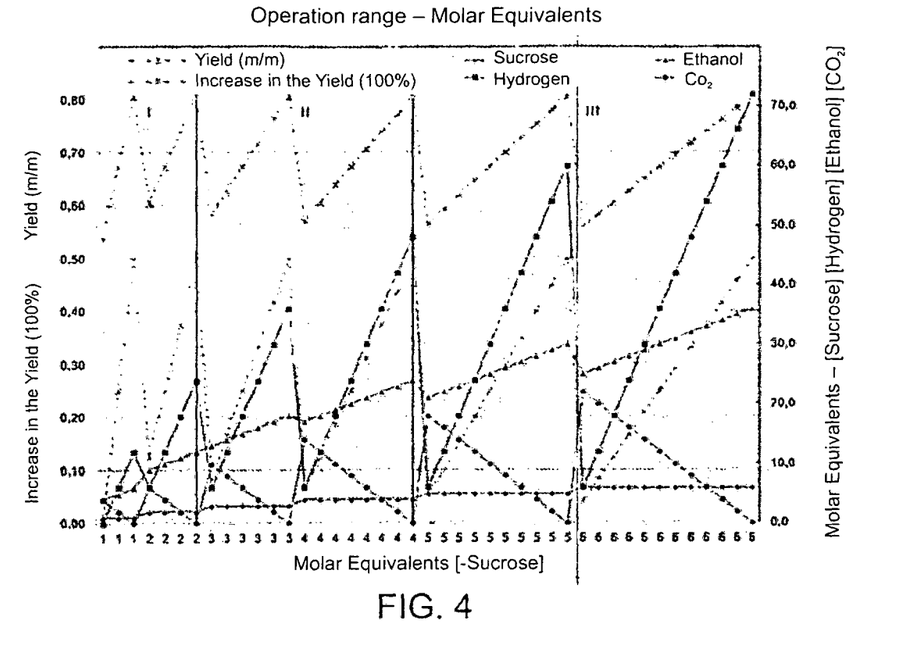
FIG. 4 refers to a graph containing the operation ranges based on Molar Equivalents of the present invention, containing the curve limits for sucrose, hydrogen, ethanol, carbon dioxide, massic (m/m) yield and increase in massic yield with respect to the G-L (%) maximum massic theoretical yield for sucrose, according to equation (3)

Particularly, the process of the invention consists in inoculating adequate concentrations of atomic, ionic or molecular hydrogen, said hydrogen having been produced in the pre-electrolysis or full-electrolysis condition in the microorganisms under process, in a controlled manner according to equation (7), Table 2 and FIG. 4. The batch-regime, continuous and semicontinuous fermentation processes are contemplated by the present invention, and one may adopt arrangements of bioreactors, in number and volumes, either in similar or different functions in their operational conditions of concentrations of substrates, microorganisms and availability of the hydrogen inoculum in the ionic or molecular phase.

Although one has not yet established, definitively and academically, the pathways of transformations of sugars into alcohols, in both anaerobic and aerobic regimes, in the presence of fungi or bacteria in media of abundant concentration of hydrogen, one can already follow the selective production of substances in these respiratory and fermentative processes.

Comparative experiments conducted in the present invention point to the theoretical increase in the yield of production of ethanol of up to 50%, entailing maximum massic theoretic efficiency of 0.8 m/m in the fermentation of sugars (sucrose), with the consequent reduction of the emitted carbon dioxide of up to 100%, with the yeast *Saccharomyces cerevisiae*.

In the present invention, through tests carried out, one has observed that, in the ethylic pathway of fermentation of sugars with yeasts, the two pyruvic acid molecules, originated from glycolysis, in their decarboxylation by the enzyme pyruvate decarboxylase, the releases of the two carboxyls are promoted, which subsequently reduced by Reducing Equivalents—ER/RE, by the action of hydrogen abundantly present in the medium, which can produce another acetaldehyde molecule that, dehydrogenated by the enzyme alcohol dehydrogenase in the reduction to ethanol, bringing about its selective increase (sic). As a result, there is the reduction of released carbon dioxide, as can be inferred from FIG. 3.

While the increase in the production of ethanol may reach the theoretical limit of 50%, the reduction of carbon dioxide may reach the consequent extreme theoretic level of 100% with respect to the traditional process. Further in this fermentative model, in the face of the concentrations of sugars increased in the intracellular processing, as a result of the increase in the concentration of hydrogen available, causing greater complexities of the enzymatic reactions, one can verify reductions in the kinetics of the reactions, which may entail an increase in the period of fermentation.

The hydrogen present in the fermentation medium may be in atomic, ionic or gaseous states or a mixture thereof. In order to obtain hydrogen, a hydrogen-generating system is required, and said system may comprise: (i) subjecting the fermentative medium to a pre-electrolysis electric voltage (voltage below the voltage required for electrolysis of water to occur, characterized by the ionic conditions of the wort under fermentation) or (ii) subjecting the fermentative medium to full-electrolysis voltage equal to or higher than the water-electrolysis voltage, characterized by the ionic conditions of the wort under fermentation.

In the pre-electrolysis regime, there is formation of ionic and atomic hydrogen, without gaseous hydrogen. The formation of such ionic and atomic hydrogen requires only electric voltage lower than that necessary for the occurrence of electrolysis of water, which is characterized by the ionic conditions of the wort under fermentation. This electric voltage ranges from 0.1 V to 1.24 V, preferably from 0.7 V to 1.1 V.

The systems for generation of pre-electrolysis and full-electrolysis hydrogen may occur in such a way that the voltage will be either direct or alternating, wherein the latter there may be cycles ranging from 50 to 2,000 Hz, preferably from 50 Hz to 150 Hz, or from 100 Hz to 500 Hz or from 400 Hz to 1,000 Hz.

In an embodiment of the invention, the system comprises direct current ion the full-electrolysis condition, avoiding the addition of oxygen to the wort under fermentation, in order to favor anaerobic conditions. By preference the cathode acts directly on the wort under fermentation, while the anode will be applied on another electrolyte, the latter being saline, according to two electrolytes, with media separated by ion-permeable separating membrane, the membrane being porous and made preferably from a porous material.

Upon starting the system of generating hydrogen on a reactor operating in a semicontinuous or continuous batch regime, it is important for the process to be continuously controlled by the measurements of pH, temperature, concentrations of sugars, concentration of hydrogen, concentrations of live microorganism, concentrations of alcohol, concentrations of carbon dioxide and contents and concentrations of micronutrients.

Additionally or exclusively, hydrogen in the gaseous phase may be introduced directly into the bioreactor in fermentation, by direct gushing into the wort under fermentation in the bioreactor, or through lines for feeding or circulating wort in the bioreactor. This hydrogen gas may be produced via bacterial fermentation or by algae in other parallel fermentative process, characterized by the production of hydrogen, or via electrolysis of water, outside the reactor, or it may be industrial hydrogen.

It is further pointed out that the hydrogen may be inoculated either immediately at the start of the fermentative process or before this step, that is, during the preparation of the microorganism.

The process described in the present invention reflects a behavior differentiated from the prior-art fermentative processes, since:

the high dosage of hydrogen acts as a powerful reducing agent;
it provides better yields in the concentration of alcohol;
there is no genetic modification of the microorganism;
there is a consequent reduction of the content of released carbon dioxide; and
there is alteration in the kinetics of the reaction.

Moreover, the process of the invention provides the following advantages over a conventional fermentation process:

1. it provides easy diffusion of hydrogen through the cellular membrane of the microorganism, fungus or bacterium, enabling intracellular compartments to be reached;
2. it does not influence the physiological parameters of the cell (temperature, pressure, pH and pO2)/
3. it does not interfere with the metabolic oxidation reactions, without detriment to the reactive species of ROS oxygen, and of cellular signaling;
4. high concentrations of hydrogen are well tolerated and consequently have less systemic side effects; and
5. it may be applied to fermentations in the semicontinuous and continuous batch regimes, being of easy adaptation to existing fermentation processes and equipment.

Control over process and productive yield according to the invention

According to the generic equation (7), the fermentative process will now provide and demand operational control over the process variables.

According to the generic equation (7), the fermentative process now provides and demands operational control of the process variables. The list of variables is composed by those comprised by the prior art, intended to maintain the process within the physical, chemical process standards typically used in the fermentative processes embraced by the prior art, such as pH and temperature, controls of levels, feeding and discharging, innovatively added to the controls and to the concentrations of reactants and products, including micronutrients. This control actuates during the whole production process, enabling one to guide said process within the adequate and intended operational conditions.

The control over concentrations, in the present invention, differs from controls of concentrations of soluble solids and sugars, as in the cases of VHG (Very High Gravity) fermentations, by which one obtains a concentration of alcohol of over 12% by volume, from the fermentative processing of worts with a high content of sugars, preventing damage to the microorganism or stuck and sluggish fermentation, as well as over processes where one aims at controlling or limiting the fermentation period, as a tool for productive control. In these traditional cases, the control over the concentration of sugars and microorganisms is reduced to establishing process operational limits.

Very High Gravity Fermentation is fermentation starting from high concentrations of substrates with a view to produce wines with high alcoholic contends, with typical concentration higher than 12% by volume.

Stuck and sluggish fermentation takes place when the fermentation process is interrupted, or when it reduces its kinetics dramatically, even with the existence of a substrate, as a result of stressing factors, such as excess alcoholic content or lack of structural micronutrients to the microorganism.

According to the present invention, the control over the concentrations go beyond the above-mentioned limits, being a control of biochemical, aiming at productive yield within the concepts involved by the generic equation (7).

The schematic balance of the generic and simplified equation (7) is directly linked to the limits of productive yield, considering the concentrations of substrates, sugars, live microorganism and inoculum [H], with a view to the selective production of alcohol and the consequent reduction in the production of carbon dioxide.

With a view to simplify the establishment of control regimes, three operational ranges are defined for the concentrations, starting from the concentration of substrate and hydrogen, aiming at the concentration of reduced alcohol. These definitions, however, do not delimit the invention by exemplary use of operational ranges of the process, which operates more comprehensively in the continuous control mode.

FIG. 4 shows the operation ranges based on moles of sucrose, the threshold values of the raised curves are transcribed in Table 2 below.

TABLE 2

| Operational control range | Molar Equivalents | | | | Yield [m/m] | Increase in yield % |
|---|---|---|---|---|---|---|
| | [sucrose] | [hydrogen] | [ethanol] | [CO2] | | |
| I | 1-2 | 0-24 | 4-12 | 4-0 | 0.538-0.808 | 0-50 |
| II | 3-4 | 25-48 | 13-24 | 10-0 | 0.565-0.808 | 6-50 |
| II | 5-6 | 49-72 | 25-72 | 22-0 | 0.561-0.808 | 4-50 |

Figure 5:
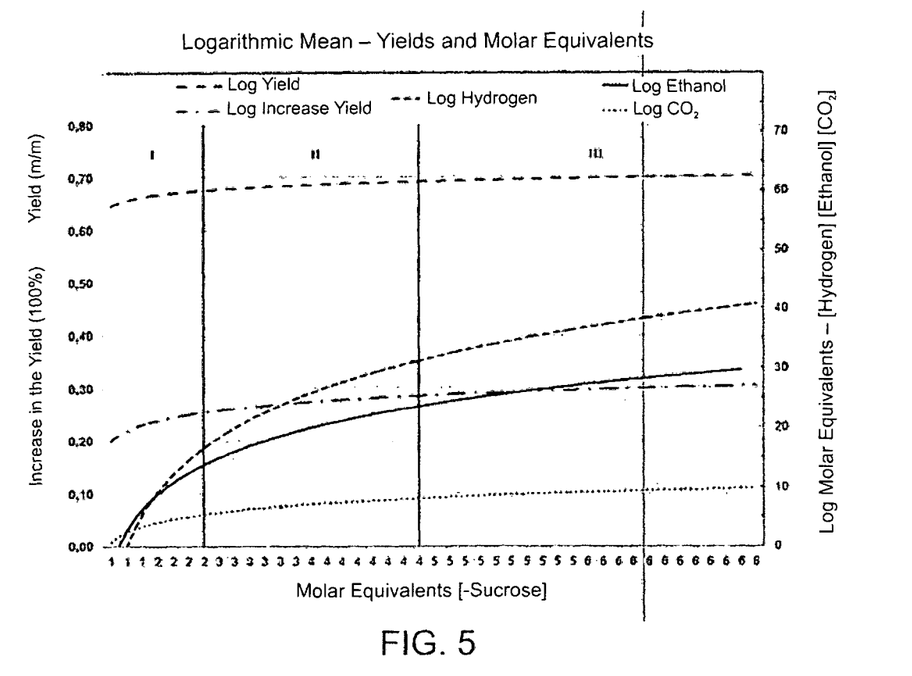
FIG. 5 refers to a graph containing the logarithmic measurements of the massic yield curves, percentage increase in the massic yield and in the concentrations in Molar Equivalents for [H], [Ethanol] and [CO2] in the present invention.

FIG. 5 shows the logarithmic measurements of the massic yield curves, percentage increase in the massic yield and in the concentrations in molar equivalent for [H], [Ethanol] and [CO2]. These values, considering he statistic conditions of the intracellular enzymatic reactions, proved to be more realistic with regard to the operationally most favorable finds.

Assays that Prove the Invention

A few assays were made for validation and evaluation of the efficacy of the process on wort under fermentation, employing sugar-cane juice and yeast microorganism of the species *Saccharomyces cerevisiae*, intensely used in the industry of fuel ethanol and beverage. An example of a process without the intention of limiting the protection scope of the invention is given below. The assay conditions and results, as well as the validation of the biochemical model, are reported later.

Example 1—Comparison Between a Conventional Fermentation with the Fermentation According to the Invention in a Pre-Electrolysis Regime In this essay one has sought the influence of hydrogen in ethyl fermentation of sugary worts, with voltage lower than that necessary to the occurrence of electrolysis of water. In the essays, including the following ones, one used, as reactants, unrefined sugar and the industrial yeast *Saccharomyces cerevisiae* in the batch fermentation.

Two bioreactors were constructed, one as a base or conventional, and the other assembled with a hydrogen generation system (using voltage with direct current of 0.95V), to produce ionic and atomic hydrogen, during the fermentation process.

In the two bioreactors, with a maximum volume of 100 liters, one added the reactants and water up to the operation volume of 50 liters.

More specifically, one made two essays in each bioreactor, fermenting 8 kg of the brown sugar substrate (fundamentally constituted by sucrose) with 5 kg of commercial yeast (fungus, *Saccharomyces cerevisiae*) in two separate lots and simultaneously.

The substrate and the fungus were dissolved and prepared before being mixed in the bioreactors, under stirring with a flat-blade stirrer at 60-90 rpm. Samples were collected from the reactors immediately after mixing the two ingredients, and the initial parameters were measured, such as soluble solids [Brix], temperature [° C.] and acidity [pH]. Measurements for Brix, temperature and pH were carried out every hour, by using a distiller and digital densimiter, adopting standard laboratory standards of this kind. No micronutrient was added to the process, with a view to isolating variables.

Table 3 specifies the ingredients used in the experiments and conditions of pre-electrolysis test. Two essays were made in two simultaneous reactors.

TABLE 3

Ingredients and Conditions of the (pre-electrolysis) Tests

| Characteristics | Conventional process | Process of the invention |
|---|---|---|
| Reactor volume | ~100 liters | ~liters |
| Fermented volume | 50 liters | 50 liters |
| Yeast - Fungus | Commercial Fleishmann *Saccharomyces cerevisiae* | Commercial Fleishmann *Saccharomyces cerevisiae* |
| Yeast mass | 5 kg | 5 kg |
| Concentration of yeast | 10% mass/volume | 10% mass/volume |
| Substrate | Brown sugar | Brown sugar |
| Substrate mass | 8 kg | 8 kg |
| Concentration of substrate | 16% mass/volume | 16% mass/volume |
| Velocity of stirring | 50-60 RPM | 80-100 RPM |
| Electric voltage | — | 0.95 Volt |
| Room temperature | 25° C. | 25° C. |

Table 4 specifies the equipment employed for controlling the parameters of pH, temperature, ° Brix and concentration of ethanol. In the tests one observed the variations in the parameters for the control of the fermentation.

TABLE 4

Equipment and Conditions of Tests

| Type | Magnitude measured | Time of sampling | Volume of the sample |
|---|---|---|---|
| pH meter | pH | Every hour | Drops |
| Thermometer | Temperature | Every hour | Thermocouple |
| Soluble solids | Brix | Every hour | Drops |
| Distiller | Separation of ethanol | Every two hour | 25 cm3 |
| Densitometer | Concentration of ethanol | Every two hour | Completed for 50 cm3 |

The results achieved in these two experiments are described in Table 5 below.

Table 5—Results achieved in the fermentation of a bioreactor containing a hydrogen generation system. in pre-electrolysis regime and a conventional bioreactor.

TABLE 5

Data and Results

Wort-Brown sugar  Valor: Test 1 Volume = 50 L  Sugar = 8 Kg
                         Test 2 V/C =0.95 V/1.2 A  Yeast = 5 Kg

| Time | Soluble solids °Bx | | Ethanol °GL | | Temperature ° C. | | Acidity pH | | Milk of lime added ml | | Corrected acidity pH | |
|---|---|---|---|---|---|---|---|---|---|---|---|---|
| h | Conv. | Inv. | Conv. | Inv. | Conv. | Inv. | Conv. | Inv. | Conv. | Inv. | Conv. | Inv. |
| 0 | 15.01 | 15.71 | 0.00 | 0.00 | 24.5 | 24.6 | 4.70 | 4.56 | | | | |
|   | 15.55 | 15.60 | 0.00 | 0.00 | 25.6 | 25.9 | 4.56 | 4.38 | | | | |
| 1 | 13.99 | 14.68 | x | x | 27.2 | 27.2 | 3.98 | 4.02 | | | | |
|   | 13.95 | 14.01 | x | x | 28.6 | 28.8 | 3.98 | 3.98 | 100 | 100 | 4.29 | 4.29 |
| 2 | 10.40 | 12.47 | 3.46 | 2.74 | 29.6 | 30.1 | 3.73 | 3.85 | 100 | | 4.05 | |
|   | 10.30 | 11.23 | 4.18 | 3.58 | 32.1 | 31.7 | 4.10 | 4.18 | | | | |

TABLE 5-continued

Data and Results

| | | | | | | | | | | | |
|---|---|---|---|---|---|---|---|---|---|---|---|
| 3 | 7.85 | 10.20 | x | x | 33.0 | 32.0 | 3.90 | 3.83 | 100 | | 4.08 |
| | 7.41 | 9.30 | x | x | 35.6 | 32.3 | 3.93 | 4.11 | 100 | 4.24 | |
| 4 | 5.00 | 8.16 | 6.82 | 5.46 | 35.4 | 33.6 | 3.82 | 4.13 | 150 | 4.20 | |
| | 3.99 | 8.06 | 7.28 | 5.58 | 37.8 | 31.7 | 4.13 | 4.04 | | | |
| 5 | 4.13 | 6.87 | x | x | 35.1 | 34.6 | 4.36 | 4.13 | | | |
| | 4.28 | 6.75 | x | x | 36.9 | 31.9 | 4.21 | 3.94 | 100 | | 4.15 |
| 6 | 3.91 | 5.94 | 7.24 | 6.82 | 34.0 | 32.7 | 4.38 | 4.14 | | | |
| | 3.93 | 5.14 | 7.50 | 7.10 | 35.7 | 32.5 | 4.24 | 4.16 | | | |
| >22 | 3.91* | 4.60* | 7.38* | 8.10* | 25.0 | 31.8 | 4.61 | 4.09 | | | |
| | 4.69* | 4.71* | 7.46* | 8.04* | 26.0 | 26.3 | 4.46 | 4.41 | | | |

*End of the fermentation-electric system of the fermenter according to the invention was turned off after the 6th hour. Reactors were kept in operation, with stirring, after the last measurements at the 6th hour. Residual fermentation was continued for 16 more hours.

The increase in the production of ethanol can be easily observed in the time of 6 hours, since one can verify, on average, 1.62° C. more sugar for the process of the invention. This additional sugar content may produce 1.1° GL more ethanol, if the Gay-Lussac equation (1) is used to calculate the theoretical value of conversion of sugar to ethanol.

As a result, the yield in the production of ethanol, directly read on Table 5, increased by 6.8% and 8.3% as compared with the traditional theoretic value expected (Gay-Lussac yield) having the same experimental criteria and yield calculations. The increase in the concentration of ethanol and the reduction observed in the release of carbon dioxide were accompanied by alterations in the chemical kinetics, which shows that the simplified biochemical model can be applied.

Example 2—Comparison Between a Conventional Fermentation and the Fermentation According to the Invention in Full-Electrolysis Regime In this essay, one inserted into the two bioreactors (the base one and that of the present invention) 9 kg of brown sugar with 6 kg of industrial yeast, Saccharomyses cerevisiae.

The tow bioreactors were used in example 1, one as a base or conventional reactor and the other equipped with a hydrogen generation system, were the same as employed in example 2. In this example, one employed the electric voltage of 1.6V—Full-Electrolysis regime, producing ionic and gaseous hydrogen, during the fermentation process.

Table 6 specifies the ingredients used in the experiments and conditions of the test for full electrolysis.

TABLE 6 ingredients and conditions of the tests in full electrolysis

| Characteristics | Conventional process | Process of the invention |
|---|---|---|
| Reactor volume | ~100 liters | ~100 liters |
| Fermented volume | 50- liters | 50 liters |
| Yeast - fungus | Commercial Fleishmann Saccharomyces cerevisiae | Commercial Fleishmann Saccharomyces cerevisiae |
| Yeast mass | 6 kg | 6 kg |
| Concentration of yeast | 12% mass/volume | 12% mass/volume |
| Substrate | Brown sugar | Brown sugar |
| Substrate mass | 9 kg | 9 kg |
| Concentration of substrate | 18% mass/volume | 18% mass/volume |
| Velocity of stirring | 50-60 RPM | 80-100 RPM |
| Electric voltage | — | 1.6 Volt |
| Room temperature | 25° C. | 25 C. |

One collected samples from the reactors immediately after the addition of the ingredients, and the initial parameters were measured, such as soluble solids [Brix], temperature [° C.] and acidity [pH]. Measurements of Brix, temperature, pH and alcoholic concentration were carried out every hour. No micronutrient was added to the processes, with a view to isolating variables. Only one test was made with the two bioreactors.

The results of the tests for this experiment are described in tables 7 and 8.

Tables 7 and 8—Results achieved in the fermentation of a bioreactor containing a hydrogen generation system in full electrolysis and a conventional bioreactor.

TABLE 7

Conventional Fermenation-Base
Environmental and conventional conditions

| Hour | °Bx | Ethanol | Temp | pH | □Et/□Bx+ | □B/□t | □Et/□t | □T/□t | □pH/□t | □Et/□Bx G-L+ |
|---|---|---|---|---|---|---|---|---|---|---|
| 0 | 19.2 | 0.00 | 26.8 | 4.56 | 0.00 | 0.00 | 0.00 | 0.00 | 0.00 | 0.682 |
| 1 | 17.83 | 1.78 | 29.6 | 4.04 | 1.299 | 1.37 | 1.78 | 2.8 | -0.52 | 0.682 |
| 2 | 14.4 | 4.26 | 32.5 | 3.79 | 0.723 | 3.43 | 2.48 | 2.9 | -0.25 | 0.682 |
| 3 | 10.32 | 6.46 | 33.5 | 4.1 | 0.539 | 4.08 | 2.20 | 1.0 | 0.31 | 0.682 |
| 4 | 8.38 | 7.94 | 33.5 | 4.05 | 0.763 | 1.94 | 1.48 | 0.0 | -0.05 | 0.682 |
| 5 | 6.63 | 9.04 | 33.7 | 4.02 | 0.629 | 1.75 | 1.10 | 0.2 | -0.03 | 0.682 |
| >22* | 5.6 | 9.28 | 33.1 | 4.08 | 0.233 | 1.03 | 0.24 | -0.6 | 0.06 | 0.682 |

TABLE 8

Fermentation according to the invention
1.6 V and direct current voltage of 3.2 A a 4.9 A

| Hour | °Bx | Ethanol | Temp | pH | □Et/□Bx+ | □B/□t | □Et/□t | □T/□t | □pH/□t | □Et/□Bx G-L+ |
|---|---|---|---|---|---|---|---|---|---|---|
| 0 | 19.25 | 0.00 | 25.5 | 4.8 | 0.00 | 0.00 | 0.00 | 0.00 | 0.00 | 0.682 |
| 1 | 18.19 | 1.54 | 28.1 | 4.27 | 1.453 | 1.06 | 1.54 | 2.6 | −0.53 | 0.682 |
| 2 | 16.19 | 2.76 | 30.1 | 4.19 | 0.610 | 2.00 | 1.22 | 2.0 | −0.08 | 0.682 |
| 3 | 14.78 | 3.54 | 31.4 | 4.08 | 0.553 | 1.41 | 0.78 | 1.3 | −0.11 | 0.682 |
| 4 | 13.98 | 4.28 | 32.2 | 4.03 | 0.925 | 0.80 | 0.74 | 0.8 | −0.05 | 0.682 |
| 5 | 13.53 | 4.66 | 32.7 | 4.01 | 0.844 | 0.45 | 0.38 | 0.5 | −0.02 | 0.682 |
| >22* | 13.12 | 4.88 | 32.9 | 4.23 | 0.537 | 0.41 | 0.22 | 0.2 | 0.22 | 0.682 |

*End of the fermentation-Electric system of the fermenter according to the invention was turned of after the 6th hour. Reactors were kept operating, with stirring after the last measurements at the 6th hour. Residual fermentation was continued for another 16 hours.

+Note, the values for (□Et/□Bx), refer to the partial yields, according to the G-L yield. For sucrose, the maximum yield is of 0.538 m/m and 0.682 v/v, according to values of the last right column, in both tables 7 and 8.

As a result, the yield in the production of ethanol in the bioreactor of the present invention was of 17% to 20% above the maximum traditional theoretic value expected (Gay-Lussac yield), as can be observed more clearly in Table 11.

For the partial values, one knows that the analytic methods bear errors, between preparation of samples and continuance of the fermentative process, even in the collected sample, which may cause significant diversions when the moments of sampling have periods of greater kinetics of the fermentative reaction in course.

Results and Validation of the Biochemical Model

With a view to present the above results in a better way, the tables below explain the values referring to the partial production of ethanol, during the process, and at the end of the fermentative process, always accompanied by the values of the bioreactor according to the invention and of the values obtained in the conventional process, or base bioreactor. It is pointed out that these values shown are obtained directly and not only from the results achieved during the essays.

TABLE 9

Essay 1: at 0.95 V (Pre-electrolysis); 1.2 A DC
Conventional reactor in environmental and conventional conditions

| | □Bx | | □Ethanol | | □Et/□Bx | | Increase Yield | |
|---|---|---|---|---|---|---|---|---|
| Houra | Conv. | Inv. | Conv. | Inv. | Conv. | Inv. | Conv. % | Inv. % |
| 0 | 0.00 | 0.00 | 0.00 | 0.00 | 0.000 | 0.000 | 0.0% | 0.0% |
| 2 | 4.61 | 3.24 | 3.46 | 2.74 | 0.751 | 0.846 | 110.1% | 124.0% |
| 4 | 10.01 | 7.55 | 6.82 | 5.46 | 0.681 | 0.723 | 99.9% | 106.0% |
| 6 | 11.10 | 9.77 | 7.24 | 6.82 | 0.652 | 0.698 | 95.6% | 102.4% |
| 22 | 11.10 | 11.11 | 7.38 | 8.04 | 0.665 | 0.724 | 97.5% | 106.1% |
| Final | 11.10 | 11.11 | 7.38 | 8.10 | 0.665 | 0.729 | 97.5% | 106.9% |

TABLE 10

Essay 2: at 0.95 V (Pre-electrolysis); 1.2 A DC
Conventional bioreactor in environmental and conventional conditions

| | □Bx | | □Ethanol | | □Et/DBx | | Increase Yield | |
|---|---|---|---|---|---|---|---|---|
| Hour | Conv. | Inv. | Conv. | Inv. | Conv. | Inv. | Conv. | Inv. |
| 0 | 0.00 | 0.00 | 0.00 | 0.00 | 0.000 | 0.000 | 0.0% | 0.0% |
| 2 | 5.25 | 4.37 | 4.18 | 3.58 | 0.796 | 0.819 | 116.7% | 120.1% |
| 4 | 11.56 | 7.54 | 7.28 | 5.58 | 0.630 | 0.740 | 92.3% | 108.5% |

TABLE 10-continued

Essay 2: at 0.95 V (Pre-electrolysis); 1.2 A DC
Conventional bioreactor in environmental and conventional conditions

| | □Bx | | □Ethanol | | □Et/DBx | | Increase Yield | |
|---|---|---|---|---|---|---|---|---|
| Hour | Conv. | Inv. | Conv. | Inv. | Conv. | Inv. | Conv. | Inv. |
| 6 | 11.62 | 10.46 | 7.50 | 7.10 | 0.645 | 0.679 | 94.6% | 99.5% |
| 22 | 10.86 | 10.89 | 7.46 | 8.04 | 0.687 | 0.738 | 100.7% | 108.3% |
| Final | 10.86 | 10.89 | 7.46 | 8.04 | 0.687 | 0.738 | 100.7% | 108.3% |

TABELA 11

Assay 3: a 1.6 V (Full Electrolysis); 3.2 A a 4.9 A DC
conventional bioreactor in environmental
and conventional Conditions

| | □B/Dt | | □Etanol | | □Et/DBx | | Aumento Rendimento | |
|---|---|---|---|---|---|---|---|---|
| Hora | Conv. | Inv. | Conv. | Inv. | Conv. | Inv. | Conv. | Inv. |
| 0 | 0.00 | 0.00 | 0.00 | 0.00 | 0.000 | 0.000 | 0.0% | 0.0% |
| 1 | 1.37 | 1.06 | 1.78 | 1.54 | 1.299 | 1.453 | 190.5% | 213.0% |
| 2 | 4.80 | 3.06 | 4,26 | 2.76 | 0.888 | 0.610 | 130.1% | 132.3% |
| 3 | 8.88 | 4.47 | 6.46 | 3.54 | 0.727 | 0.553 | 106.7% | 116.1% |
| 4 | 10.82 | 5.27 | 7.94 | 4.28 | 0.734 | 0.925 | 107.6% | 119.1% |
| 5 | 12.57 | 5.72 | 9.04 | 4.66 | 0.719 | 0.844 | 105.5% | 119.5% |
| 22 | 13.60 | 6.13 | 9.28 | 4.88 | 0.682 | 0.537 | 100.1% | 116.7% |
| Final | 13.60 | 6.13 | 9.28 | 4.88 | 0.682 | 0.796 | 100.1% | 116.7% |

One observes that in tables 9, 10 and 11 the values in the columns "Increase Yield" exhibit accumulated and final partial values, always higher for those obtained according to the invention. The final values, of 6.9% and 8.3%, with respect to the maximum fermentative yield, considering the prior art, of 0.538 mass/mass or 0.682 volume/volume, obtained in the respective essays 1 and 2, operating in pre-electrolysis voltage regime and direct current, DC, per se only qualify the invention in its productive limits. The concentrations of [sucrose], [hydrogen] and [yeast] are in the range from low (I) to medium (II) Molar Equivalents.

The values presented in Table 11 relating to the essay 3 for the "Increase Yield", for both partial and final, are eloquent and definitive. One can see that the final or accumulated value in the essay 3 of 16.7% reflects the prompt response to the process according to the invention, to the increase in the concentration of hydrogen in atomic, ionic and gaseous state, with a behavior expected by FIGS. 4 and 5.

The biochemical model in the first two essays, plus the values and peculiarities presented by the essay 3, proves to be technically validated in its technological and innovative limits.

As expected, the essay 3, operating with Molar Equivalents in the moderate range (II), had the reaction kinetics substantially altered, since the process had reduction in the rate of production of ethanol by the sugar consumed (☐Et/☐Bx), still with a large amount of sugar present in the medium. The availability of micronutrients, chiefly of N (nitrogen), in the face of the high microbial activity, is fundamental to the increase in biomass, which is a natural phenomenon in a fermentative process. The lack chiefly of nitrogen prevents multiplication of the fermentative microorganism, being a stressing fermentation condition.

In addition to the analyses made and reported herein, the reduction in the emission of carbon dioxide during the process was verified qualitatively, with clear evidence of the reduction, as compared to the process developed simultaneously in the conventional bioreactor. Those skilled in the art have these means—appearance and smell—for this nature of evaluation.

In Table 12, one presents the summaries of the fermentative results, considering the volume of ethanol produced in the three essay.

TABLE 12

Summary of Essays 1,2 e 3

| Table-Summary | 1 | | 2 | | 3 | |
|---|---|---|---|---|---|---|
| Magnitudes | Conventional | Invention | Conventional | Invention | Conventional | Invention |
| Variation Sugar ☐Bx | 11.10 | 11.11 | 10.86 | 10.89 | 13.60 | 6.13 |
| Variation Ethanol ☐ ☐t | 7.38 | 8.10 | 7.46 | 8.04 | 9.28 | 4.88 |
| Volume Ethanol-Liter | 3.69 | 4.05 | 3.73 | 4.02 | 4.64 | 2.44 |
| Volume Ethanol/☐Bx | 0.33 | 0.36 | 0.34 | 0.37 | 0.34 | 0.40 |

Thus, one considers validated the process of the invention, according to the results achieved in laboratory essays.

The reduction of emission of carbon dioxide, as a result of the biochemical process, with the selective increase in the production of alcohol, emerges as a technological complement of the great environmental and operational importance. A few economical and environmental advantages provided by the invention can be listed as follows:

1—direct economic increase, with the increase in the production of alcohol;
2—increase in the production without causing an increase in the planted area;
3—reduction in the production of carbon dioxide;
4—process equipment does not require adjustments as to the volume of production, as well as the bioreactors and the distillation equipment;
5—reduction in the sizing and consumption of energy, in the equipment of recovering alcohol dragged by carbon dioxide in the fermentation;
6—increase in the Carbon Credit with an increase in the production of alcohol and with the reduction of carbon dioxide released;
7—targeted technology with the improvement in the environment. The ethanol is completed as a green fuel and greater economic feasibility.

The invention claimed is:

1. A process for microbial fermentation of sugary substrates, comprising applying electric voltage to at least two electrodes applied to a wort to generate hydrogen and inoculating the generated hydrogen into a microorganism of a genera fungus or a bacterium present in suspension in the wort under fermentation or in an immobilized bed, said wort containing sugars and microorganisms.

2. The process according to claim 1, wherein the at least two electrodes include at least one cathode and one anode, said cathode being applied directly to the wort and the anode being applied to another electrolyte.

3. The process according to claim 1, further comprising adding:
   5% to 30% (mass/volume) of sugary substrates; and
   5% to 25% (mass/volume) of microorganisms of the genera fungus or the bacterium.

4. The process according to claim 1, wherein the hydrogen is in an atomic state, an ionic state, a gaseous state, or a mixture thereof.

5. The process according to claim 1, further comprising subjecting the at least two electrodes to a regime of pre-electrolysis of water with electric voltage ranging from 0.1 V to 1.24 V to produce ionic and atomic hydrogen.

6. The process according to claim 5, wherein the electric voltage applied to the at least two electrodes takes place in a direct or alternating regime with cycles ranging from 50 Hz to 2000 Hz.

7. The process according to claim 6, wherein the electric voltage applied to the at least two electrodes takes place in an alternating regime with cycles ranging from 50 Hz to 150 Hz, 100 Hz to 500 Hz, or 400 Hz to 1000 Hz.

8. The process according to claim 5, wherein the pre-electrolysis regime comprises a voltage ranging from 0.7 V to 1.1 V.

9. The process according to claim 1, further comprising subjecting the at least two electrodes to a regime of full electrolysis of water with electric voltage ranging from 1.24 V to 30 V to produce atomic, ionic, gaseous hydrogen or mixtures thereof.

10. The process according to claim 9, wherein the full-electrolysis regime comprises an electric voltage ranging from 1.24 V to 20 V.

11. The process according to claim 10, wherein the electric voltage applied to the at least two electrodes takes place in a direct or alternating regime with cycles ranging from 50 Hz to 2000 Hz.

12. The process according to claim 11, wherein the electric voltage applied to the at least two electrodes takes place in an alternating regime with cycles ranging from 50 Hz to 150 Hz, 100 Hz to 500 Hz, or 400 Hz to 1000 Hz.

13. The process according to claim 1, wherein the sugars include polysaccharides and monosaccharides with trioses, tetroses, pentoses, hexoses sucrose, glucose, fructose, xylose, or mixtures thereof.

14. The process according to claim 1, wherein the microorganisms of the genus fungus present in the wort are selected from the genus *Saccharomyces* and the species of *Schizosaccharomyces pompe, Pichia stipites, Torula, Candida schehatae*, of naturally-occurring lines, or especially selected or adapted, or recombinant, flocculating lines.

15. The process according to claim 1, wherein the microorganisms of the bacterium genus present in the wort are selected from the species of the genus *Zymomonas mobilis, Escherichia coli* and *Clostridium*, of naturally occurring lines, or especially selected and adapted, or recombinant, flocculating lines.

16. The process according to claim 1, wherein micronutrients include nitrogen, phosphorus, potassium, magnesium, calcium, zinc, manganese, copper, iron, cobalt, sulfur, iodine, or a mixture thereof.

17. The process according to claim 1, wherein the hydrogen in a gaseous state is produced outside of a bioreactor by applying electric voltage ranging from 1.24 V to 30 V in a regime of pre-electrolysis of water and is then inserted directly by gushing into the bioreactor.

18. The process according to claim 1, wherein the fermentative process takes place in a continuous process, a semicontinuous process, or a batch process.

19. The process according to claim 1, further comprising continuously controlling for at least one of pH, temperature, control of levels, feeding and discharge, concentrations of reactants, concentration of hydrogen, concentrations of live microorganisms, concentration of alcohol, concentrations of carbon dioxide, and contents of concentration of micronutrients.

* * * * *